United States Patent [19]

Maignan et al.

[11] Patent Number: 4,898,864
[45] Date of Patent: Feb. 6, 1990

[54] BICYCLIC AROMATIC COMPOUNDS, A PROCESS FOR THEIR PREPARATION AND THEIR USE IN COSMETICS AND HUMAN AND VETERINARY MEDICINE

[75] Inventors: Jean Maignan, Tremblay les Gonesse; Gerard Lang, Saint Gratien; Gérard Malle, Villiers sur Morin; Philippe Vingler, Gif-sur-Yvette, all of France

[73] Assignee: L'Oreal, Paris, France

[21] Appl. No.: 112,860

[22] Filed: Oct. 27, 1987

[30] Foreign Application Priority Data

Oct. 27, 1986 [FR] France ................. 86 14901

[51] Int. Cl.$^4$ ............................................. C07C 59/76
[52] U.S. Cl. ............................. 514/237.5; 514/255;
514/330; 514/423; 514/532; 514/567; 514/569;
514/617; 514/622; 514/719; 514/730; 562/460
[58] Field of Search ............. 562/460; 514/569, 255,
514/237.5, 330, 423, 569, 730, 719, 532, 617,
622; 424/401

[56] References Cited

U.S. PATENT DOCUMENTS 3,994,920 11/1976 Sulkowski ............. 540/473
4,550,197 10/1985 Shippey ................. 562/460

OTHER PUBLICATIONS

Fu et al., "A Modified Approach to the Synthesis of 5—and 6—Methylbenz Anthracenes", *Organic Prep. & Proc.*, 14(3), 169–175, (1982).
Witrak et al., *J. of Org. Chem.*, 51(24), pp. 4499–4507, Nov. 28, 1986.

Primary Examiner—Prince E. Willis
Assistant Examiner—Kathleen Markowski
Attorney, Agent, or Firm—Cushman, Darby & Cushman

[57] ABSTRACT

Bicyclic aromatic compound having the formula

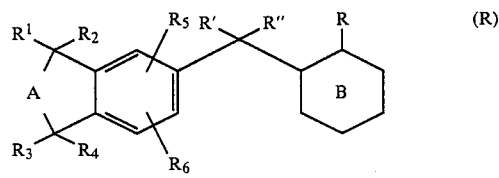

wherein
$R_1$, $R_2$, $R_3$ and $R_4$ represent hydrogen or alkyl, at least two of $R_1$–$R_4$ radicals being other than hydrogen,
A represents methylene or dimethylene; when A represents dimethylene, $R_1$ and $R_3$ together can form a methylene or dimethylene radical,
$R_5$ and $R_6$ represent hydrogen, halogen, lower alkyl, lower alkoxy or hydroxy,
R' represents hydrogen, hydroxy, alkoxy, $C_1$–$C_4$ cicyloxy or amino,
R" represents hydrogen or lower alkoxy, or R' and R" together form an oxo, methano or hydroxyimino radical;
B represents cyclohexyl, cyclohexenyl, cyclohexadienyl or phenyl, substituted or not,
R represents —CH$_2$OH or —COR$_7$,
R$_7$ represents hydrogen, —OR$_8$ or

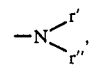

$R_8$ represents hydrogen, $C_1$–$C_{20}$ alkyl, monohydroxyalkyl, polyhydroxyalkyl, aryl, aralkyl or a sugar residue.
r' and r" represent hydrogen, alkyl, monohydroxyalkyl, polyhydroxyalkyl, aryl or benzyl, the residue of an amino acid or an aminated sugar, or taken together form a heterocycle, and
the salts of the compound of formula I and their optical isomers as well as the tautomeric forms of the compounds of formula I with the exception of 2-[(5,8-methano-5,6,7,8-tetrahydro-2-naphthyl) carbonyl] benzoic acid.

The compounds are useful in the treatment of the hair and skin having an oily appearance.

15 Claims, No Drawings

BICYCLIC AROMATIC COMPOUNDS, A PROCESS FOR THEIR PREPARATION AND THEIR USE IN COSMETICS AND HUMAN AND VETERINARY MEDICINE

The present invention relates to new bicyclic aromatic compounds, to a process for their preparation and to their use in cosmetic compositions and in human and veterinary medicine.

The compounds according to the present invention, due to their inhibiting activity on the synthesis of lipids, are of great interest in cosmetics for the treatment of the scalp and skin exhibiting an oily appearance.

These compounds also exhibit activity in the topical and systemic treatment of dermatologic disorders having an inflammatory component.

The bicyclic aromatic compounds of the present invention can be represented by the formula:

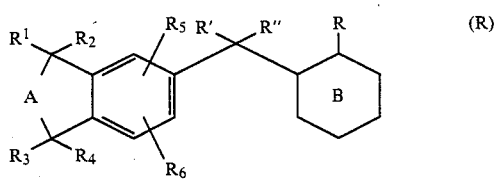

(R)

wherein
$R_1$, $R_2$, $R_3$ and $R_4$ each independently represent hydrogen or lower alkyl, at least two of radicals $R_1$-$R_4$ being other than hydrogen;
A represents methylene or dimethylene substituted or not by lower alkyl; when A represents dimethylene, $R_1$ and $R_3$ together can form methylene or dimethylene;
$R_5$ and $R_6$ represent hydrogen, halogen, lower alkyl, lower alkoxy or hydroxy;
R' represents hydrogen, hydroxy, lower alkoxy, $C_1$–$C_4$ acyloxy or amino;
R" represents hydrogen or lower alkoxy, or R' and R" taken together form an oxo radical (=O), a methano radical (=$CH_2$) or hydroxyimino (=N—OH);
B represents a cyclohexyl, cyclohexenyl, cyclohexadienyl or a phenyl ring, substituted or not;
R represents —$CH_2OH$ or —$COR_7$, wherein
$R_7$ represents hydrogen, —$OR_8$ or

$R_8$ represents hydrogen, alkyl having 1–20 carbon atoms, monohydroxyalkyl, polyhydroxyalkyl, aryl or aralkyl optionally substituted or the residue of a sugar;
r' and r" represent hydrogen, lower alkyl, monohydroxyalkyl optionally interrupted by a heteroatom, polyhydroxyalkyl, aryl or benzyl optionally substituted, the residue of an amino acid or aminated sugar, or r' and r" taken together form a heterocycle; and
the salts of said compounds of formula I and their optical isomers, as well as the tautomeric forms of the compounds of formula I, with the exception of 2-[(5,8-methano-5,6,7,8-tetrahydro-2-naphthyl)carbonyl]benzoic acid.

By lower alkyl is meant a radical having from 1 to 6 carbon atoms.

By lower alkyl or alkyl having up to 20 carbon atoms is meant principally methyl, ethyl, propyl, isopropyl, butyl, tertiobutyl, 2-ethylhexyl, octyl, dodecyl, hexadecyl and octadecyl.

By monohydroxyalkyl is meant a radical having 2 to 6 carbon atoms and principally 2-hydroxyethyl, 2-hydroxypropyl or 2-hydroxyethoxyethyl.

By polyhydroxyalkyl is meant a radical containing 3 to 6 carbon atoms and 2 to 5 hydroxy groups, such as 2,3-dihydroxypropyl, 1,3-dihydroxy-2-propyl or the residue of pentaerythritol.

Representative lower alkoxy radicals include, particularly, methoxy, isopropoxy, butoxy and tertiobutoxy.

By residue of a sugar is meant a residue derived from, for example, glucose, mannose, erythrose or galactose.

Representative aminated sugar residues are those derived from glucosamine, galactosamine, mannosamine or meglumine.

When the radical B is a substituted phenyl ring, the substituents can be lower alkyl, halogen or an alkoxy, in the 3,4,5, or 6 position.

When the r' and r" radicals after taken together with the nitrogen atom to which they are attached they form a heterocycle. The heterocycle is preferably piperidino, piperazino, morpholino, pyrrolidino or 4-(2-hydroxyethyl) piperazino.

When the compounds of the present invention are provided in the form of salts, it is a question either of salts of zinc, an alkali metal or an alkaline earth metal, or of an organic amine when they bear at least one free acid function, or salts of a mineral or organic acid, principally the hydrochloride, hydrobromide or citrate when they bear at least one amine function.

The compounds of the present invention can be provided in tautomeric form when R' and R" taken together form an oxo radical and R represents a carboxylic acid function or an amide function.

Thus, the compounds of formula 11 below can be provided in cyclic lactone form, III.

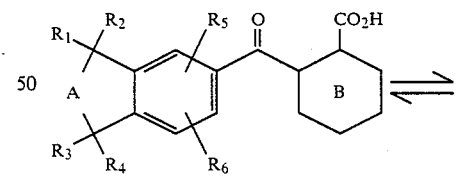

(II)

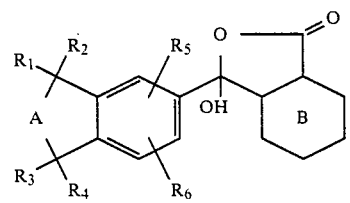

(III)

Also the compounds of formula IV can be provided in lactam tautomer form of formula V.

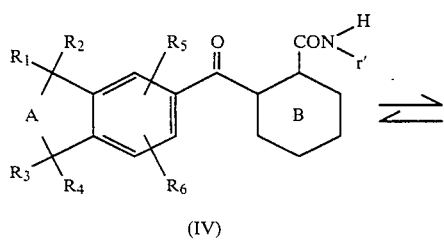

(IV)

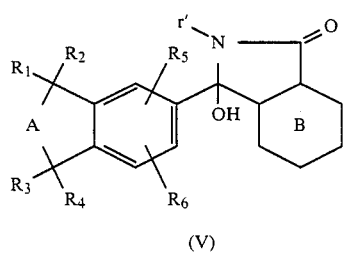

(V)

Particularly preferred compounds of formula I include those corresponding to the following formula:

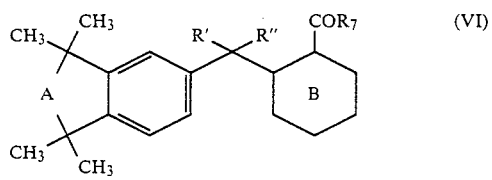

wherein
R' and R" taken together form an oxo radical (=O) or R' represents hydroxy and R" represents hydrogen;
A represents —(CH$_2$)$_2$— or

B represents phenyl or cyclohexyl;
R$_7$ represents OR$_8$ or

R$_8$ represents hydrogen or alkyl having 1–12 carbon atoms;
r' represents hydrogen or monohydroxyalkyl; and
r" represents alkyl having 1–8 carbon atoms, monohydroxyalkyl, optionally interrupted by a heteroatom, or polyhydroxyalkyl, or r' and r" taken together with the nitrogen atom to which they are attached form 4-(2-hydroxyethyl) piperazinyl, or the salts of the compounds of formula VI.

Representative compounds of formula I, according to the present invention, include the following:
(1) 2-[(5,5,8,8-tetramethyl-5,6,7,8-tetrahydro-2-naphthyl) carbonyl]benzoic acid;
(2) N-ethyl 2-[(5,5,8,8-tetramethyl-5,6,7,8-tetrahydro-2naphthyl)carbonyl]benzamide;
(3) methyl 2-[(5,5,8,8-tetramethyl-5,6,7,8-tetrahydro-2naphthyl)carbonyl]benzoate;
(4) 2'ethylhexyl 2-[(5,5,8,8-tetramethyl-5,6,7,8-tetrahydro-2-naphthyl)carbonyl]benzoate;
(5) sodium 2-[(5,5,8,8-tetramethyl-5,6,7,8-tetrahydro-2naphthyl)carbonyl]benzoate;
(6) zinc 2-[(5,5,8,8-tetramethyl-5,6,7,8-tetrahydro-2naphthyl)carbonyl]benzoate;
(7) 2-[(5,5,8,8-tetramethyl-5,6,7,8-tetrahydro-2-naphthyl) hydroxymethyl]benzaldehyde;
(8) 2-[(5,5,8,8-tetramethyl-5,6,7,8-tetrahydro-2-naphthyl) hydroxymethyl]phenyl carbinol;
(9) 2-[(5,5,8,8-tetramethyl-5,6,7,8-tetrahydro-2-naphthyl) hydroxymethyl]benzoic acid;
(10) N-4'-(2-hydroxyethyl)-2-piperazino[(5,5,8,8-tetramethyl-5,6,7,8-tetrahydro-2-naphthyl)carbonyl]benzamide;
(11) 2-[(5,5,8,8-tetramethyl-5,6,7,8-tetrahydro-2-naphthyl) ethoxymethyl]benzoic acid;
(12) 2-[(1,1,2,3,3-pentamethyl-5-indanyl]benzoic acid;
(13) 2-[2-(1,1,2,3,3-pentamethyl-5-indanyl)-2-ethenyl]benzoic acid;
(14) 2-[(1,1,2,3,3-pentamethyl-5-indanyl)carbonyl]benzoic acid;
(15) N-ethyl 2-[(1,1,2,3,3-pentamethyl-5-indanyl)carbonyl]benzamide;
(16) ethyl 2-[(1,1,2,3,3-pentamethyl-5-indanyl)carbonyl]benzoate;
(17) 2'-ethylhexyl 2-(1,1,2,3,3-pentamethyl-5-indanyl) carbonyl]benzoate;
(18) sodium 2-[(1,1,2,3,3-pentamethyl-5-indanyl)carbonyl]benzoate;
(19) N-4'-(2-hydroxyethyl) piperazino 2-[(1,1,2,3,3-pentamethyl-5-indanyl)carbonyl]benzamide;
(20) 2-[(1,1,3,3-tetramethyl-5-indanyl)hydroxymethyl]benzoic acid;
(21) 2-[(1,1,3,3-tetramethyl-5-indanyl)carbonyl]benzoic acid;
(22) N-ethyl 2-[(1,1,3,3-tetramethyl-5-indanyl)carbonyl)]benzamide;
(23) N 4'-(2-hydroxyethyl) piperazino 2-[(1,1,3,3-tetramethyl-5-indanyl)carbonyl]benzamide;
(24) zinc 2-[(1,1,3,3,-tetramethyl-5-indanyl)carbonyl]benzoate;
(25) ethyl 2-[(5,8-methano-5,6,7,8-tetrahydro-2-naphthyl) carbonyl]benzoate;
(26) N-ethyl 2-[(5,8-methano-5,6,7,8-tetrahydro-2-naphthyl) carbonyl]benzamide;
(27) 2-[(5,8-methano-5,6,7,8-tetrahydro-2-naphthyl) hydroxymethyl]benzoic acid;
(28) 2-[(1,4-dimethoxy-5,8-methano-5,6,7,8-tetrahydro-2-naphthyl)hydroxymethyl]benzoic acid;
(29) 2-[(1,4-dimethoxy-5,8-methano-5,6,7,8-tetrahydro-2-naphthyl)carbonyl]benzoic acid;
(30) N-ethyl 2-[(1,4-dimethoxy-5,8-methano-5,6,7,8-tetrahydro-2-naphthyl)carbonyl]benzamide;
(31) N, N-di n-butyl 2-[(5,5,8,8-tetramethyl-5,6,7,8-tetrahydro-2-naphthyl)carbonyl]benzamide;
(32) 2-[(5,5,8,8,-tetramethyl-5,6,7,8-tetrahydro-2-naphthyl) carbonyl]cyclohexane carboxylic acid;
(33) 2-[(1,1,2,3,3-pentamethyl-5-indanyl)carbonyl]-1-cyclohexene-1-carboxylic acid;
(34) N,N-di(2-hydroxyethyl) 2-[(5,5,8,8-tetramethyl-5,6,7,8-tetrahydro-2-naphthyl)carbonyl]benzamide;
(35) sodium 2-[(5,5,8,8-tetramethyl-5,6,7,8-tetrahydro-2-naphthyl)carbonyl]cyclohexane carboxylate;
(36) 2-[(1,1,2,3,3-pentamethyl-5-indanyl)carbonyl]cyclohexane carboxylic acid;
(37) ethyl 2-[(5,5,8,8,-tetramethyl-5,6,7,8-tetrahydro-2naphthyl)carbonyl]cyclohexane carboxylate;

(38) 2-[(5,5,8,8-tetramethyl-5,6,7,8-tetrahydro-2-naphthyl) hydroxymethyl]cyclohexane carboxylic acid;

(39) sodium 2-[(5,5,8,8-tetramethyl-5,6,7,8-tetrahydro-2naphthyl)hydroxymethyl]cyclohexane carboxylate;

(40) ethyl 2-[(5,5,8,8-tetramethyl-5,6,7,8-tetrahydro-2naphthyl)carbonyl]benzoate;

(41) 2-[(5,5,8,8-tetramethyl-5,6,7,8-tetrahydro-2-naphthyl) methyl]benzoic acid;

(42) zinc 2-[(5,5,8,8-tetramethyl-5,6,7,8-tetrahydro-2naphthyl)carbonyl]benzoate; and

(43) zinc 2-[(5,5,8,8-tetramethyl-5,6,7,8-tetrahydro-2naphthyl)carbonyl]cyclohexane carboxylate.

The present invention also relates to a process for preparing the bicyclic aromatic compounds of formula I.

These compounds can be prepared in accordance with the following reaction scheme:

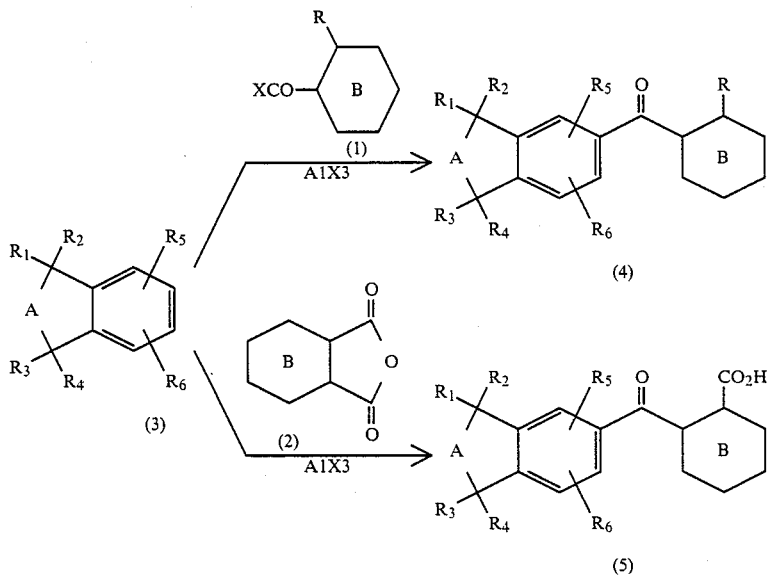

X = Cl or Br

These compounds result, in a first condensation stage, effected under Friedel-Crafts reaction conditions, of either a substituted acid halide (1), or an anhydride of structure (2) on a bicyclic aromatic compound of formula (3).

Preferably, the condensation reaction is carried out using an internal anhydride of structure (2) in the presence of a Lewis acid such as aluminum chloride or tin chloride in a chlorinated solvent such as 1,2-dichloroethane.

Representative initial bicyclic aromatic compounds of formula (3) include 1,1,4,4-tetramethyl-1,2,3,4 naphthalene (described in JACS, 62, 36–44, 1940); 1,4-methano-1,2,3,4tetrahydro naphthalene or benzonorbornene (described in JOC, 32 893–901, 1967); 5,8-dihydroxy-1,4-methano-1,2,3,4-tetrahydro naphthalene (commerical product); 1,1,3,3-tetramethyl indane; and 1,2,3,3-pentamethyl indane (described in French Pat. No. 1.392.804).

Starting with compounds of formulas (4) and (5), and principally starting with keto-acids of formula (5), there can be produced, in accordance with the reaction scheme, other forms of the compounds of the present invention.

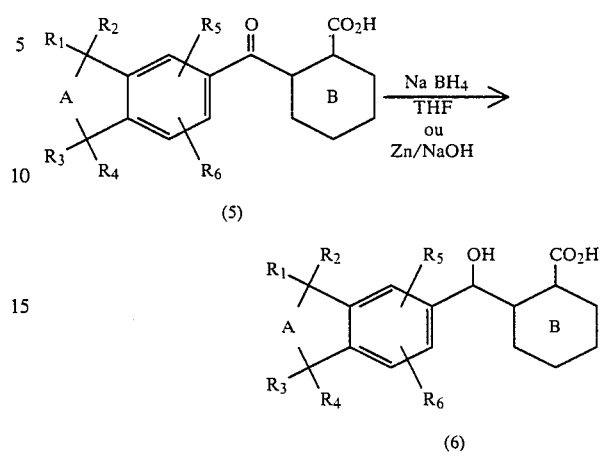

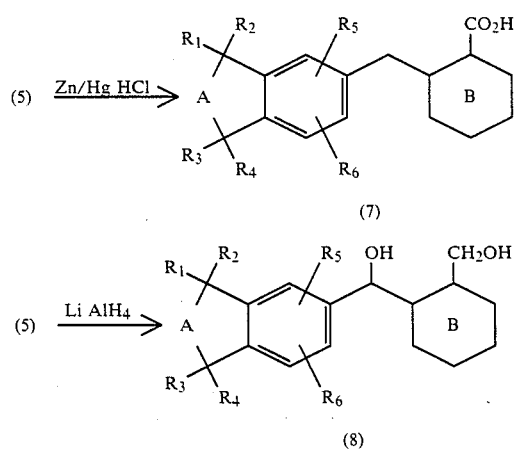

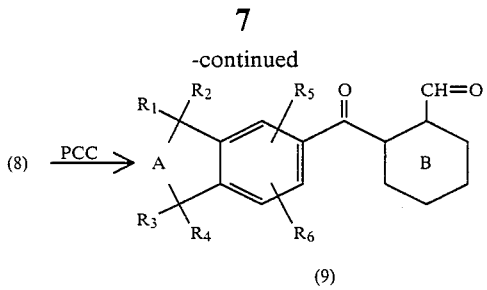

Thus, on reduction using sodium borohydride, in a solvent such as tetrahydrofuran or even with zinc in an alkaline medium, secondary alcohols of formual (6) can be produced.

Carrying out a Clemmensen reduction using zinc amalgam in the presence of HCl, produces compounds of formula (7).

Effecting a reduction reaction using lithium aluminum hydride in tetrahydrofuran produces diols of formula (8).

Starting with these diols, and oxidizing them with pyridinium chlorochromate (PCC) provides keto-aldehydes of formula (9).

The acyloxy derivatives of the compounds of formula I, (R'=acyloxy and R"=H) are obtained by reacting an active form of the acid, such as an anhydride or acid chloride, with a compound of the present invention wherein R'=OH and R"=H.

The alkoxy derivatives of the compounds of formula I, (R'=alkoxy and R"=H) are obtained in the same way starting with compounds of formula I, (R'=OH and R"=H) in accordance with known methods.

The compounds of formula I, wherein R' and R" together form a methano radical (=CH$_2$), are obtained by the action of methyl triphenyl phosphonium bromide, in a basic medium, on carbonyl compounds of formula I wherein R' and R" taken together form an oxo radical.

The compounds of formula I wherein R' and R" together form a hydroxyimino radical are obtained by the reaction of hydroxylamine hydrochloride on corresponding carbonyl compounds in an organic solvent, such as ethanol, in the presence of a mineral base such as sodium bicarbonate or an organic base such as triethylamine.

These hydroxyimino derivatives provide, on reduction with zinc in an acetic medium, the corresponding amines, (R'=NH$_2$ and R"=H).

The compounds of formula I, in accordance with the present invention, exhibit excellent activity in the test described by J. Girard and A. Barbier, Int. Journal of Cosmetic Science 2, 315–329 (1980) and M. Gauci and J. Oustrin, Int. Journal of Cosmetic Science 3, 227–232 (1982). These authors have, in effect, shown that the "in vivo" test of incorporating labelled glucose can be retained as an orientation test for nonhormonal antiseborrheics since this test accounts for the inhibiting activity of the synthesis of lipids.

Moreover, it is known that an increase in the secretion of sebum produces dermatologic conditions such as seborrhea, pellicles, oily skin, oily hair, whiteheads and blackheads. These chronic phenomena of pilo-sebaceous disorders concern especially the face, the chest and the back.

Moreover, the acids of formula I, in accordance with the invention in which (R=—CO$_2$H), exhibit a bactericide activity on acne germs.

These compounds are then indeed particularly appropriate for the treatment of dermatologic diseases linked to a disorder involving the production of, or the excessive secretion of, sebum, as well as for dermatologic disease or others having an inflammatory component, and principally acne vulgaris, acne with comedos or polymorphous acne, senile acne, solar acne and medication-induced or occupational acne.

The present invention also relates to a new medicinal composition, intended principally for the treatment of the above-mentioned disorders, characterized by the fact that it comprises, in a pharmaceutically acceptable support, at least one compound of formula I and/or one of its isomers, and/or one of its tautomeric forms, and/or one of its salts.

As the support for the compositions, any conventional support can be employed, the active component being found in the dissolved state, or in the dispersed state in the support or vehicle.

The compositions can be administered to a person suffering from said disorders, enterally, parenterally, topically or ocularly. When administered enterally, the medicinal composition can be provided in the form of tablets, gelules, lozenges, syrups, suspensions, solutions, powders, granules or emulsions.

When administered parenterally, the composition can be provided in the form of solutions or suspensions for perfusion or injection.

The compounds in accordance with the present invention are generally administered at a daily dose of about 0.1 mg/kg to 10 mg/kg of body weight.

When administered topically, the pharmaceutical compositions, based on the compounds of the present invention, are provided in the form of salves, tinctures, creams, ointments, powders, plasters, impregnated tampons, solutions, emulsions, lotions, gels, sprays or suspensions.

These topically applicable compositions can be provided either in anhydrous form or in aqueous form, depending on the clinical indications.

When the compounds of the present invention are employed topically, good activity of these compounds is observed on a very large range of dilution; there can be employed, principally, active component concentrations ranging from 0.01 to 10 percent by weight. It is possible, however, to employ even higher concentrations when it is necessary for a particular therapeutic application; however, the preferred concentrations of the active component range between 0.1 and 5 weight percent, based on the total weight of the composition.

The compounds of the present invention are also usefully employed in the field of cosmetics, in particular for capillary and body hygiene and principally for the treatment of skin having a tendency towards acne, for promoting hair growth, for combatting hair loss, for combatting the oily appearance of the skin or hair and in the prevention or treatment of the harmful effects of the sun.

The present invention also relates to a cosmetic composition comprising, in a cosmetically acceptable vehicle or support, at least one compound of formula I, or one of its salts, said composition being provided principally-in the form of a lotion, a gel, a soap or a shampoo.

The pharmaceutical or cosmetic compositions in accordance with the present invention can also contain inert additives or even pharmacodynamically or cosmetically active additives and principally: hydrating agents such as thiomorpholinone and its derivatives or urea; antiseborrheic agents such as S-carboxymethyl-cysteine, S-benzylcysteamine and their derivatives and tioxolone; anti-acne agents such as benzoyl peroxide; antibiotics such as erythromycin and its esters, neomycin, tetracyclines or 4,5-polymethylene-3-isothiazolinones; agents promoting the growth of hair such as "Minoxidil" (2,4-diamino-6-piperidino- 3-pyrimidine oxide) and its derivatives, Diazoxide (7-chloro-3-methyl-1,2,4-benzothiadiazine-1,1-dioxide) and Phenytoin (5,5-diphenyl-2,4-imidazolinedione) or even oxapropanium iodide; steroidal and non-steroidal anti-inflammatory agents; carotenoids and principally β-carotene; anti-psoriasis agents such as anthralin and its derivatives and 5,8,11,14-eicosatetraynoic and 5,8,11-triynoic acids, their esters and amides.

The compositions according to the present invention can also contain flavor improving agents, preservatives, stablizers, humidity regulators, pH regulators, osmotic pressure modifiers, emulsifiers, UV-A and UV-B filters, antioxidants such as α-tocopherol, butylhydroxyanisole and buhylhydroxytoluene.

The following non-limiting examples are given to illustrate the preparation of the active compounds of formula I of the present invention as well as compositions containing these active compounds.

EXAMPLE I

Preparation of 2-[(5,5,8,8-tetramethyl-5,6,7,8-tetrahydro-2-naphthyl)-carbonyl]benzoic acid Compound of formula I wherein $A=-(CH_2)_2-$; $R_1=R_2=R_3=R_4=CH_3$; $R_5=R_6=H$; R', R''=oxo; B=phenyl; and $R=CO_2H$ To a suspension of 9.41 g (0.05 mole) of 1,1,4,4-tetramethyl-1,2,3,4-tetrahydronaphthalene and 7.46 g (0.05 mole) of phthalic anhydride in 100 cm³ of anhydrous 1,2-dichloroethane, there are added by portions, 13.3 g (0.1 mole) of anhydrous aluminum chloride in a manner so as to maintain the temperature below 30° C. After stirring for 1 hour at ambient temperature, the reaction mixture is poured into 100 cm³ of ice water. The organic phase is decanted. The aqueous phase is extracted twice again with 150 cm³ of dichloroethane. The dichloroethane phases are combined, washed with water, dried on sodium sulfate and then concentrated under reduced pressure. The resulting crude solid is taken up in 250 ml of boiling hexane, filtered after cooling to +5° C. and recrystallized in 200 cm³ of toluene. After drying under a vacuum at 80° C., 13.5 g of white crystals of 2-[(5,5,8,8-tetramethyl-5,6,7,8-tetrahydro-2-naphthyl)carbonyl]benzoic acid are obtained whose melting point is 187° C. The NMR¹H 250 MHz and IR spectra confirm the expected structure.

Elemental analysis: $C_{22}H_{24}O_3$.

|  | C | H | O |
|---|---|---|---|
| Calculated | 78.54 | 7.19 | 14.27 |
| Found | 78.82 | 6.93 | 14.25 |

EXAMPLE II

Preparation of 2-[(1,1,2,3,3-pentamethyl,-5-indanyl) carbonyl]benzoic acid

Compound of formula I wherein A=

$R_1=R_2=R_3=R_4=CH_3$; $R_5=R_6=H$; R', R''=oxo; B=phenyl and $R=CO_2H$

To a suspension of 13.2 g (0.07 mole) of 1,1,2,3,3-pentamethyl indane and 10.37 g (0.07 mole) of phthalic anhydride in 150 cm³ of anhydrous 1,2-dichloroethane, these are added by portions, 16 g (0.12 mole) of anhydrous aluminum chloride in a manner so as to maintain the temperature below 30° C. After stirring for 1 hour at ambient temperature, the reaction mixture is poured into 100 cm³ of ice water. The organic phase is decanted. The aqueous phase is extracted twice again with 100 cm³ of dichloroethane.

The dichloroethane phases are combined, washed with water, dried on sodium sulfate and then concentrated under reduced pressure. The resulting crude solid is taken up in hexane, filtered, and recrystallized in ethylacetate. After drying, 15.5 g of white crystals of 2-[(1,1,2,3,3-pentamethyl-5indanyl)carbonyl]benzoic acid are obtained whose melting point is 205° C. The NMR¹H 80 MHz and IR spectra conform to the expected structure.

Elemental analysis: $C_{22}H_{24}O_3$.

|  | C | H | O |
|---|---|---|---|
| Calculated | 78.54 | 7.19 | 14.27 |
| Found | 78.50 | 7.20 | 14.15 |

EXAMPLE III

Preparation of 2-[(5,5,8,8-tetramethyl 5,6,7,8-tetrahydro-2-naphthyl)carbonyl]cyclohexane carboxylic acid Compound of formula I wherein $A=-(CH_2)_2-$; $R_1=R_2=R_3=R_4=CH_3$; $R_5=R_6=H$; R',R''=oxo; B=cyclohexyl; and $R=CO_2H$ To a suspension of 16.95 g (0.09 mole) of 1,1,4,4-tetramethyl-1,2,3,4-tetrahydronaphthalene and 13.9 g (0.09 mole) of cishexahydrophthalic anhydride in 150 cm³ of anhydrous 1,2-dichloroethane, there are added by portions 20 g (0.15 mole) of anhydrous aluminum chloride in a manner so as to maintain the temperature below 30° C. After stirring for 1 hour at ambient temperature, the reaction mixture is poured into 100 cm³ of ice water. The organic phase is decanted. The aqueous phase is extracted with 150 cm³ of dichloroethane.

The dichloroethane phases are combined, washed with water, dried on sodium sulfate and then concentrated under reduced pressure. The resulting crude solid is taken up in lukewarm hexane, filtered, and recystallized in ethylacetate. After drying, 20.7 g of white crystals of 2-[(5,5,8,8-tetramethyl-5,6,7,8-tetrahydro-2-naphthyl)carbonyl]cyclohexane carboxylic acid are obtained whose melting point is 173° C. The NMR¹H 80 MHz and IR spectra conform to the expected structure.

Elemental analysis: $C_{22}H_{30}O_3$.

|  | C | H | O |
|---|---|---|---|
| Calculated | 77.15 | 8.83 | 14.02 |
| Found | 76.93 | 8.89 | 13.97 |

EXAMPLE IV

Preparation of 2-[(1,1,2,3,3-pentamethyl-5-indanyl) carbonyl]-1-cyclohexene-1-carboxylic acid Compound of formula I wherein A=

$R_1=R_2=R_3=R_4=CH_3$; $R_5=R_6=H$; R', R''=oxo; B=cyclohexenyl; and $R=CO_2H$

To a suspension of 5.88 g (0.031 mole) of 1,1,2,3,3-indane and 5 g (0.031 mole) of 3,4,5,6-tetrahydrophthalic anhydride in 60cm³ of anhydrous 1,2-dichloroethane, there are added by portions, 8.3 g (0.06 mole) of anhydrous aluminum chloride in a manner so as to maintain the temperature below 30° C. After stirring for 2 hours, the reaction mixture is poured into 40 cm³ of ice water. The organic phase is decanted. The aqueous phase is extracted twice again with 150 cm³ of dichloroethane.

The dichloroethane phases are combined, washed with water, dried on sodium sulfate and then concentrated under reduced pressure. The resulting crude solid is purified by chromatography on silica 60 gel, eluted with dichloromethane and crystallized in hexane. After filtering and drying, 4.8 g of white crystals of 2-[(1,1,2,3,3-pentamethyl-5-indanyl)carbony]-1-cyclohexene-1-carboxylic acid are obtained whose melting point is 153° C. The NMR¹H 250 MHz and ¹³C spectra in deuterochloroform as well as IR spectra (KBr and dichloromethane) correspond to the lactol cyclized form.

Elemental analysis: $C_{22}H_{28}O_3$.

|  | C | H | O |
|---|---|---|---|
| Calculated | 77.61 | 8.29 | 14.10 |
| Found | 77.94 | 8.47 | 13.53 |

EXAMPLE V

Preparation of 2-[(1,4-dimethoxy-5,8-methano-5,6,7,8-tetrahydro-2-naphthyl)carbonyl]benzoic acid.

Compound of formula I wherein $A=-(CH_2)_2-$; $R_1$ and $R_3=-CH_2-$; $R_2=R_4=H$; $R_5=R_6=OCH_3$; R', R''=oxo; B=phenyl; and $R=-CO_2H$ To a suspension of 2.25 g (11 mmoles) of 5,8-dimethoxy-1,4-methano-1,2,3,4-tetrahydronaphthalene and 1.63 g (11 mmoles) of phthalic anhydride in 40 ml of anhydrous 1,2-dichloroethane, there are added by portions in about 30 minutes, 2.93 g (22 mmoles) of anhydrous almminum chloride. After stirring over night at ambient temperature, the reaction mixture is poured into 40 cm³ of ice water. The organic phase is decanted. The aqueous phase is extracted twice again with 100 cm³ of dichloroethane.

The dichloroethane and dichloromethane phases are combind, washed with water, dried on sodium sulfate and then evaporated to dryness. The resulting solid is purified twice by chromatography on silica 60 gel in a 50/50 dichloromethane/tetrahydrofuran eluant mixture. After evaporation and drying, the isolated solid is taken up in isopropyl ether. After filtering and drying 0.4 g of 2-[(1,4 -dimethoxy-5,8-methano-5,6,7,8-tetrahydro-2-naphthyl) carbonyl]benzoic acid in the form of a white powder is obtained whose melting point is 213° C. The NMR¹H 80 MHz spectrum conforms to the expected structure.

Elemental analysis: $C_{21}H_{20}O_5$.

|  | C | H | O |
|---|---|---|---|
| Calculated | 71.38 | 5.72 | 22.70 |
| Found | 71.18 | 5.76 | 22.67 |

EXAMPLE VI

Preparation of 2-[(5,5,8,8-tetramethyl-5,6,7,8-tetrahydro-2-naphthyl) hydroxymethyl]phenylcarbinol.

Compound of formula I wherein $A=-(CH_2)_2-$; $R_1=R_2=R_3=R_4=CH_3$; $R_5=R_6=H$; R'=OH; R''=H; B=phenyl and $R=CH_2OH$ To a suspension of 350mg (9 mmoles) of lithuim aluminum hydride in 10 cm³ of tetrahydrofuran, cooled to 0° C, there is slowly added a solution of 1 g (3 mmoles) of 2-[(5,5,8,8-tetramethyl-5,6,7,8-tetrahydro-2-naphthyl)carbonyl]benzoic acid in 20 cm³ of anhydrous tetrahydrofuran. After stirring for 1 hour and permitting the reaction mixture to return to ambient temperature, the reaction mixture is cooled to 0° C, acidified by the slow addition of 0.1N HCl and extracted with ethyl ether. The organic phase is washed with water, dried on sodium sulfate and evaporated to dryness.

The resulting crude diol is purified by chromatography on silica 60 gel and eluted with a 97/3 dichloromethane/ethyl acetate mixture. After evaporation, a colorless oil is obtained which is crystallized in hexane. After filtering and drying 0.8 g of white crystals of 2-[(5,5,8,8-tetramethyl-5,6,7,8-tetrahydro-2-naphthyl)hydroxymethyl]phenyl carbinol is obtained whose melting point is 95–98° C. The NMR¹H 80 MHz spectra corresponds to the expected structure.

Elemental analysis: $C_{22}H_{28}O_2$.

|  | C | H | O |
|---|---|---|---|
| Calculated | 81.44 | 8.70 | 9.86 |
| Found | 81.48 | 8.46 | 9.82 |

EXAMPLE VII

Preparation of 2'-ethylhexyl-2[(5,5,8,8-tetramethyl-5,6,7,,8-tetrahydro-2-naphthyl) carbonyl]benzoate Compound of formula I wherein $A=-(CH_2)_2-$; $R_1=R_2=R_3=R_4=CH_3$; $R_5=R_6=H$; R', R''=oxo; B=phenyl; and $R=-CO_2C_8H_{17}$ A solution of 4.2 g (0.0125 mole) of 2-[(5,5,8,8-tetramethyl-5,6,7,8-tetrahydro-2-naphthyl)carbonyl]benzoic acid, described in Example I, and 3.26 g (0.025 mole) of 2-ethyl-1-hexanol in 100 cm³ of toluene containing 0.1 cm³ of 98% sulfuric acid is heated for 8 hours a reflux with azeotropic distillation of the water formed.

The reaction mixture is then cooled to ambient temperature, thoroughly washed with water and concentrated under reduced pressure. The resulting crude oil is rapidly purified by chromatography on silica 60 gel and eluted with a 50/50 toluene/dichloromethane mixture. After evaporation and drying, 4.1 g of 2′-ethylhexyl 2-[(5,5,8,8-tetramethyl-5,6,7,8tetrahydro-2-naphthyl)-carbonyl benzoate in the form of a colorless liquid are obtained. The NMR$^1$H 80 MHz and IR spectra correspond to the expected structure.

Elemental analysis: $C_{30}H_{40}O_3$.

|  | C | H | O |
|---|---|---|---|
| Calculated | 80.31 | 8.99 | 10.70 |
| Found | 80.46 | 8.91 | 10.75 |

EXAMPLE VIII

Preparation of ethyl 2-[(1,1,2,3 3-pentamethyl-5-indanyl)carbonyl]benzoate

Compound of formula I wherein A=

$R_1=R_2=R_3=R_4=CH_3$; $R_5=R_6=H$; R′, R″=oxo; B=phenyl; and R=$-CO_2C_2H_5$

A solution of 2.4 g (7.1 mmoles) of 2-[(1,1,2,3,3-pentamethyl-5-indanyl)carbonyl]benzoic acid, described in Example II, in 80 cm$^3$ of ethyl alcohol containing 0.1 cm$^3$ of 98% sulfuric acid, is heated for 12 hours at reflux. The solution is then concentrated under reduced pressure. The crude ester is dissolved in 100 cm$^3$ of ethyl ether. The etherified solution is washed with sodium bicarbonate and then with water, dried on sodium sulfate and finally evaporated to dryness. After drying, 2.5 g of ethyl 2-[(1,1,2,3,3-pentamethyl-5-indanyl)carbonyl]benzoate in the form of a colorless oil are obtained which slowly crystallizes at ambient temperature to give a white solid whose melting point is 56–57° C. The NMR$^1$H 80 MHz and IR spectra conform to the expected structure.

Elemental analysis: $C_{24}H_{28}O_3$.

|  | C | H | O |
|---|---|---|---|
| Calculated | 79.09 | 7.74 | 13.17 |
| Found | 79.12 | 7.85 | 12.98 |

EXAMPLE IX

Preparation of methyl 2-[(5,5,8,8-tetramethyl-5,6,7,8-tetrahydro-2-naphthyl)-carbonyl]benzoate Compound of formula I wherein A=$-(CH_2)_2$ $R_1=R_2=R_3=R_4=CH_3$; $R_5=R_6=H$; R′,R″=oxo; B=phenyl; and R=$-CO_2CH_3$ A solution of 3.36 g (0.01 mole) of 2-[(5,5,8,8-tetramethyl-5,6,7,8-tetrahydro-2-naphthyl)carbonyl]benzoic acid, described in Example I, in 125 cm$^3$ of methyl alcohol containing 0.1 cm$^3$ of 98% sulfuric acid is heated for 24 hours at reflux. The solution is concentrated under reduced pressure. The crude ester is dissolved in 150 cm$^3$ of ethyl ether, washed with sodium bicarbonate and water. After drying on sodium sulfate, the ether phase is evaporated to dryness. The resulting solid is recrystallized in a minimum of hexane. After drying, 2,2 g of white crystals of methyl 2-[(5,5,8,8-tetramethyl-5,6,7,8-tetrahydro-2-naphthyl)carbonyl]benzoate are obtained whose melting point is 77–78° C. The NMR$^1$H 80 MHz and IR spectra correspond to the expected structure.

Elemental analysis: $C_{23}H_{26}O_3$.

|  | C | H | O |
|---|---|---|---|
| Calculated | 78.82 | 7.48 | 13.70 |
| Found | 78.93 | 7.50 | 13.79 |

EXAMPLE X

Preparation of N-ethyl 2-[(5,5,8,8-tetramethyl-5,6,7,8-tetrahydro-2-naphthyl)-carbonyl]benzamide Compound of formula I wherein A=$-(CH_2)_2-$; $R_1=R_2=R_3=R_4=CH_3$; $R_5=R_6=H$; R′, R″=-oxo; B=phenyl; and R=$-CONHC_2H_5$ To a solution of 3.36 g (0.01 mole) of 2-[(5,5,8,8-tetramethyl-5,6,7,8-tetrahydro-2-naphthyl)carbonyl]benzoic acid in 30 cm$^3$ of anhydrous dichloromethane, there is added 0.55 cm$^3$ (6 mmoles) of phosphorus trichloride. The mixture is heated for three hours at reflux. The reaction mixture is then cooled to +5° C. and 2 cm$^3$ (0.03 mole) of anhydrous ethylamine are added. Stirring is maintained for 30 minutes at +5° C. and then for 1 hour while permitting the reaction mixture to return to ambient temperature. The reaction mixture is then diluted to 100 cm$^3$ by the addition of dichloromethane and washed with diluted HCl and then with water. The dichloromethane phase is dried on sodium sulfate and then concentrated under reduced pressure. The resulting crude product is purified by chromatography on silica 60 gel in a 5/3/2 toluene/dichloromethane/ethyl acetate eluant mixture, followed by recrystallization in isopropyl ether. After drying, 1.75 g of white crystals of N-ethyl 2-[(5,5,8,8-tetramethyl-5,6,7,8-tetrahydro-2-naphthyl)carbonyl]benzamide are obtained whose melting point is 201° C.

The NMR$^1$H 250 MHz and $^{13}$C. in deuterochloroform spectra as well as the IR spectra (KBr and dichloromethane) correspond to the cyclized lactam form.

Elemental analysis: $C_{24}H_{29}NO_2$.

|  | C | H | N | O |
|---|---|---|---|---|
| Calculated | 79.30 | 8.04 | 3.85 | 8.80 |
| Found | 79.32 | 8.01 | 3.80 | 8.69 |

EXAMPLE

Preparation of N,N-di-n-butyl 2-(5,5,8,8-tetramethyl-5,6,7,8-tetrahydro-2-naphthyl)carbonyl]benzamide Compound of formula I wherein A=$-(CH_2)_2-$; $R_1=R_2=R_3=R_4=CH_3$; $R_5=R_6=H$; R′,R″=oxo; B=phenyl; and R=$-CON(C_4H_9)_2$ To a solution of 1.68 g (5 mmoles) of 2-[(5,5,8,8-tetramethyl-5,6,7,8-tetrahydro-2-naphthyl)carbonyl]benzoic acid in 20 cm$^3$ of anhydrous dichloromethane, there is added 0.22cm³ (2.5 mmoles) of phosphorus trichloride. The mixture is heated for 3 hours at reflux. After cooling to +5° C., 2.6 cm³ (15 mmoles) of dibutylamine are added. Stirring is maintained for 30 minutes at +5° C., and then for 1 additional hour so as to permit the reaction mixture to return to ambient temperature. The reaction mixture is then diluted to about 80 cm³ by the addition of dichloromethane. It is then transferred to a decanting ampoule and washed first with diluted HCl and then with water. The dichloromethane phase is dried on sodium sulfate and then concentrated under reduced pressure. The resulting crude product is purified by chromatography on silica 60 gel in a 5/3/2 toluene/dichloromethane/ethyl acetate eluant mixture. After evaporation and drying under a vacuum a 80° C., 0.6 g of N,N-di-n-butyl 2-[(5,5,8,8-tetramethyl-5,6,7,8-tetrahydro-2-naphthyl) carbonyl]benzamide in the form of a colorless thick oil is obtained. The NMR¹H 80 MHz and IR spectra correspond to the expected structure.

Elemental analysis: $C_{30}H_{41}NO_2$ 0.25 $H_2O$.

|  | C | H | N | O |
|---|---|---|---|---|
| Calculated | 79.69 | 9.25 | 3.10 | 7.96 |
| Found | 79.48 | 9.37 | 3.16 | 7.97 |

EXAMPLE XII

Preparation of 2-[(5,5,8,8-tetramethyl-5,6,7,8-tetrahydro-2-naphthyl)carbonyl]benzaldehyde Compound of formula I wherein A=—$(CH_2)_2$—; $R_1=R_2=R_3=R_4=CH_3$; $R_5=R_6=H$; R', R''=oxo; B=phenyl; and R=—CHO To a solution of 1 g (3 mmoles) of 2-[(5,5,8,8-tetramethyl-5,6,7,8-tetrahydro-2-naphthyl)hydroxymethyl]phenyl carbinol, described in Example VI, in 20 cm³ of dry dichloromethane and stirred at ambient temperature, there are added 2.3 g (10.6 mmoles) of pyridinium chlorochromate. Stirring is continued for 1 hour and 30 minutes at a temperature lower than or equal to 28° C. After dilution to about 200 cm³ with dichloromethane, 50 g of silica 60 gel are added and the mixture is filtered on "Celite".

The filtrate is concentrated under reduced pressure. The resulting crude solid is purified by chromatography on silica 60 gel and eluted with dichloromethane. After evaporation and drying under a vacuum at 70° C., 0.3 g of 2-[(5,5,8,8-tetramethyl-5,6,7,8-tetrahydro-2-naphthyl)carbonyl]benzaldehyde in the form of a white solid is obtained whose melting point is 145° C. The NMR¹H 80 MHz spectrum conforms to the expected structure.

Elemental analysis: $C_{22}H_{24}NO_2$.

|  | C | H | O |
|---|---|---|---|
| Calculated | 82.46 | 7.55 | 9.99 |
| Found | 82.88 | 7.37 | 9.82 |

EXAMPLE XIII

Preparation of 2-[(5,5,8,8-tetramethyl-5,6,7,8-tetrahydro-2-naphthyl) hydroxymethyl]benzoic acid and its lactone Compound of formula I wherein A=—$(CH_2)_2$—; $R_1=R_2=R_3=R_4=CH_3$; $R_5=R_6=H$; R'=OH; R''=H; B=phenyl; and R=—$CO_2H$.

To a solution of 2 g (8.12 mmoles) of 2-[(5,5,8,8-tetramethyl-5,6,7,8-tetrahydro-2-naphthyl)carbonyl]benzoic acid in 50 cm³ of anhydrous tetrahydrofuran, there are added, in portions, 1.82 cm³ (0.048 mmoles) of sodium borohydride. The mixture is stirred for 20 hours at ambient temperature. The mixture is then cooled to a temperature between 0 and 5° C, acidified by the slow addition of 0.1N HCl and extracted with ethyl ether. The organic phase is washed with water, dried on sodium sulfate and evaporated to dryness. The resulting crude product is rapidly purified by chromatography on silica 60 gel in dichloromethane, followed by recrystallization in hexane. After drying, 1.1 g of white crystals of the lactone of the acid 2-[(5,5,8,8-tetramethyl-5,6,7,8-tetrahydro-2-naphthyl) hydroxymethyl]benzoic acid are obtained whose melting point is 134° C.

This NMR¹H 250 MHz and ¹³C spectra as well as the IR spectra correspond to the expected structure.

Elemental analysis: $C_{22}H_{24}NO_2$.

|  | C | H | O |
|---|---|---|---|
| Calculated | 82.46 | 7.55 | 9.99 |
| Found | 82.45 | 7.60 | 10.11 |

A suspension of 0.96 g (3 mmoles) of the lactone described above in 60 cm³ of normal soda is heated for 2 hours at reflux. The resulting solution is cooled to +5° C. and then acidified by the addition of 3.5 cm³ of glacial acetic acid. The resulting precipitate is filtered, thoroughly washed with water and dried under a vacuum on potash at ambient temperature. 0.96 g of 2[(5,5,8,8-tetramethyl-5,6,7,8-tetrahydro-2-naphthyl) hydroxymethyl]benzoic acid in the form of a well crystallized and very hydrophobic white solid is obtained, which becomes gummy on heating and then returns again to a solid melting at 134° C. (transformation into the lactone). The NMR¹H 250 MHz and IR spectra conform to the expected structure.

Elemental analysis: $C_{22}H_{26}NO_3$.

|  | C | H | O |
|---|---|---|---|
| Calculated | 78.07 | 7.74 | 14.18 |
| Found | 77.97 | 7.72 | 13.89 |

EXAMPLE XIV

Preparation of sodium 2-[(5,5,8,8-tetramethyl-5,6,7,8-tetrahydro-2-naphthyl)-carbonyl]benzoate Compound of formula I wherein A=—$(CH_2)_2$—; $R_1=R_2=R_3=R_4=CH_3$; $R_5=R_6=H$; R', R''=oxo; B=phenyl; and R=CO⊕ Na⊖

1.25 g (3.73 mmoles) of 2 [(5,5,8,8-tetramethyl-5,6,7,8-tetrahydro-2-naphthyl) carbonyl]benzoic acid are suspended in 300 cm³ of bipermuted water 37.3 cm³ of 0.1 N aqueous soda (3.73 mmoles) are added and the mixture is stirred, becoming lukewarm until dissolution. The solution is filtered and then evaporated to dryness. 50 cm³ of toluene are added and the mixture is again evaporated to dryness. There are thus obtained, after drying under a vacuum at 80° C, 1.32 g of sodium 2-[(5,5,8,8-tetramethyl-5,6,7,8-tetrahydro-2-naphthyl)carbonyl]benzoate in the form of a white powder whose melting point is greater than 300° C.

EXAMPLE XV

Preparation of sodium 2-[(5,5,8,8-tetramethyl-5,6,7,8-tetrahydro-2-naphthyl)carbonyl]cyclohexane carboxylate Compound of formula I wherein $A = -(CH_2)_2-$; $R_1=R_2=R_3=R_4=CH_3$; $R_5=R_6H$; R', R"=oxo; B=cyclohexyl; $R= -CO \oplus Na \ominus$ 342.5mg (1 mmole) of 2-[(5,5,8,8-tetramethyl-5,6,7,8-tetrahydro-2-naphthyl) carbonyl]cyclohexane carboxylic acid are suspended in 150 cm³ of bipermuted water. 10cm³ of 0.1N aqueous soda (1 mmole) are added and the mixture is stirred, becoming lukewarm until dissolution. The resulting solution is then filtered and evaporated to dryness. 50 cm³ of toluene are added and the mixture is again evaporated to dryness. There is thus obtained, after drying under a vacuum at 80° C., 0.36 g of sodium 2[(5,5,8,8-tetramethyl-5,6,7,8-tetrahydro-2-naphthyl) carbonyl]cyclohexane carboxylate in the form of a solid which becomes vitreous at a temperature between 145 and 150° C.

EXAMPLE XVI

Preparation of 2-[(1,1,3,3-tetramethyl-5-indanyl) carbonyl]benzoic acid

Compound of formula I wherein $A=-(CH_2)_2-$; $R_1=R_2=R_3=R_4=CH_3$; $R_5=R_6=H$; R', R"=oxo; B=phenyl; and $R=-CO_2H$ To a suspension of 2.96 g (17 mmoles) of 1,1,3,3-tetramethyl indane and 2.52 g (17 mmoles) of phthalic anhydride in 100 cm³ of anhydrous 1,2-dichloromethane, there are added in portions, 3.4 g (25.5 mmoles) of anhydrous aluminum chloride in a manner to maintain the temperature below 30° C. After stirring for 3 hours, the reaction mixture is poured into 50 cm³ of ice water. The organic phase is decanted. The aqueous phase is again extracted twice with 50 cm³ of dichloromethane. The dichloromethane phases are combined, washed with water, dried on sodium sulfate and then concentrated under reduced pressure. The residue is taken up in 100 cm³ of lukewarm hexane, filtered after cooling to +5° C., washed twice with 50 cm³ of hexane and then recrystallized in a minimum of boiling toluene. After drying under a vacuum at 80° C, 3.1 g of white crystals of 2-[(1,1,3,3-tetramethyl-5-indanyl) carbonyl]-benzoic acid are obtained whose melting point is 194°–195° C.

The NMR¹H 80 MHz and IR spectra conform to the expected structure.

Elemental analysis: $C_{21}H_{22}O_2$.

|  | C | H | O |
|---|---|---|---|
| Calculated | 75.49 | 7.75 | 16.76 |
| Found | 75.47 | 7.67 | 16.92 |

EXAMPLE XVII

Preparation of 2-[(1,1,2,3,3-pentamethyl-5-indanyl) carbonyl] cyclohexane carboxylic acid Compound of formula I wherein A=

$R_1=R_2=R_3=R_4=CH_3$; $R_5=R_6=H$; R', R"=oxo; B=cyclohexyl; and $R=CO_2H$

To a suspension of 3.3 g (17.5 mmoles) or 1,1,2,3,3-pentamethyl indane and 2.7 g (17.5 mmoles) of cis hexahydrophthalic anhydride in 100 cm³ of anhydrous 1, 2-dichloroethane, there are added, in portions, 4.7 g (35 mmoles) of anhydrous aluminum chloride in a manner to maintain the temperature below 30° C.

After stirring for 3 hours at ambient temperature, the reaction mixture is poured into 50 cm³ of ice water. The organic phase is decanted. The aqueous phase is again extracted twice with 100 cm³ of dichloroethane. The dichloroethane phases are combined, washed with water, dried on sodium sulfate and then evaporated to dryness. The residue is taken up in 200 cm³ of lukewarm hexane, filtered after cooling to +5° C., washed three times with 100cm³ of hexane, cooled and dried under a vacuum at 70° C. 5.1 g of 2-[(1, 1, 2, 3, 3-pentamethyl-5-indanyl) carbonyl] cycohexane carboxylic acid are obtained in the form of a white solid whose melting point is 178° C.

The NMR¹H 80 MHz and IR spectra conform to the expected structure.

Elemental analysis: $C_{22}H_{30}O_3$.

|  | C | H | O |
|---|---|---|---|
| Calculated | 77.15 | 8.83 | 14.02 |
| Found | 77.21 | 9.00 | 13.56 |

EXAMPLE XVIII

Preparation of N,N-di(2-hydroxyethyl)2-[(5,5,8,8-tetramethyl-5,6,7,8-tetrahydro- 2-naphthyl) carbonyl]benzamide Compound of formula I where in $A=-(CH_2)_2-$; $R_1=R_2=R_3=R_4=CH_3$; $R_5=R_6=H$; R', R"=oxo; B=phenyl;

To a solution of 3.36 g (10 mmoles) of 2-[(5,5,8,8-tetramythyl-5,6,7,8-tetrahydrg-2-naphthyl) carbonyl]benzoic acid, described in Example I, in 30 cm³ of anhydrous dichloromethane, there is added 0.44 cm³ of phosphorus trichloride. The mixture is heated for 3 hours at reflux. After cooling to +5° C., 5.25 g (0.05 mole) of diethanoloamine are added and the mixture is stirred initially for 30 minutes at +5° C and then for 1 hour so as to permit the reaction mixture to return to ambient temperature. The reaction mixture is then diluted to about 80 cm³, transferred to a decanting ampoule, and washed first with diluted HCl and then with water. The dichloromethane phase is dried on sodium sulfate and concentrated under reduced pressure. The resulting solid is purified by chromatography on silica 60 gel in 3/2/5 ethylacetate/isopropyl alcohol/dichloromethane eluant mixture. After evaporation and drying, 3.2 g of N,N-di(2-hydroxyethyl)2-[(5,5,8,8-tetramethyl- 5,6,7,8- tetrahydro-2-naphthyl)carbonyl]benzamide are obtained in the form of a white solid, whose melting point is 116° C. The NMR$^1$H 250 MHz spectrum conforms to the expected structure.

Elemental Analysis: $C_{26}H_{33}NO_4$.

|  | C | H | N | O |
|---|---|---|---|---|
| Calculated | 73.73 | 7.85 | 3.31 | 19.11 |
| Found | 73.51 | 7.88 | 3.27 | 19.40 |

EXAMPLE XIX

Preparation of N-4'-(2-hydroxyethyl) piperazino 2-[(5,5,8,8-tetramethyl-5,6,7,8-tetrahydro-2-naphthyl) carbonyl]benzamide Compound of formula I wherein A=—(CH$_2$)$_2$—; R$_1$=R$_2$=R$_3$=R$_4$=CH$_3$; R$_5$=R$_6$=H; R', R''=oxo; B=phenyl; and

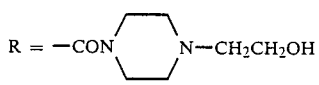

A solution of 1.68 g (5 mmoles) of 2-[(5,5,8,8-tetramethyl-5,6,7,8-tetrahydro-2-naphthyl)carbonyl]benzoic acid, described in Example I, and 0.28 cm$^3$ (3 mmoles) of phosphorous trichloride in 15 cm$^3$ of anhydrous dichloromethane is heated for 3 hours at reflux. After cooling to a temperature between 0 and +5° C, 1.4 cm$^3$ (11.4 mmoles) of N-(2-hydroxyethyl) piperazine are added and the mixture is stirred for 1 hour in the absence of light so as to permit the reaction mixture to return to ambient temperature. The reaction mixture is diluted to about 80 cm$^3$ by the addition of dichloromethane, transferred to a decanting ampoule and thoroughly washed with water. The dichloromethane phase is dried on sodium sulfate and concentrated under reduced pressure. The resulting crude solid is purified by chromatography on silica gel 60 in the absence of light, by using initially a 50/50 tetrahydrofuran/dichloromethane eluant mixture and then tetrahydrofuran alone. After evaporation and drying in the absence of light, 0.9 g of N-4'-(2-hydroxyethyl)piperazino 2-[(5,5,8,8-tetramethyl-5,6,7,8-tetrahydro-2-naphthyl) carbonyl]benzamide is obtained in the form of a white solid whose melting point is 58–60° C. The NMR$^1$H 250MHz spectrum corresponds to the expected structure.

EXAMPLE XX

Preparation of ethyl 2-[(5,5,8,8-tetramethyl-5,6,7,8-tetrahydro-2-naphthyl)-carbonyl]cyclohexane carboxylate Compound of formula I wherein A=—(CH$_2$)$_2$-R$_1$=R$_2$=R$_3$=R$_4$=CH$_3$; R$_5$=R$_6$=H; R', R''=oxo; B=cyclohexyl; R=—Co$_2$C$_2$H$_5$ A solution of 3.42 g (10 mmoles) of 2-[(5,5,8,8-tetramethyl-5,6,7,8-tetrahydro-2-naphthyl) carbonyl]cyclohexane carboxylic acid, described in Example III, in 100 cm$^3$ of ethyl alcohol containing 0.1 cm$^3$ of 98% sulfuric acid, is heated for 12 hours at reflux. The solution is concentrated under reduced pressure and the resulting crude ester is dissolved in 100 cm$^3$ of ethyl ether. The ether solution is washed with sodium bicarbonate and then with water, dried on sodium sulfate and evaporated to dryness. After drying, 3.6 g of ethyl 2-[(5,5,8,8-tetramethyl-5,6,7,8-tetrahydro-2-naphthyl)car-bonyl]cyclohexane carboxylate are obtained in the form of a colorless thick oil.

The IR and NMR$^1$H 80 MHz spectra correspond to the expected structure.

Elemental analysis: $C_{24}H_{34}O_3$.

|  | C | H | O |
|---|---|---|---|
| Calculated | 77.80 | 9.25 | 12.95 |
| Found | 77.65 | 9.29 | 12.78 |

EXAMPLE XXI

Preparation of 2-[(5,5,8,8-tetramethyl-5,6,7,8-tetrahydro-2-naphthyl) hydroxymethyl]cyclohexane carboxylic acid Compound of formula I wherein A=—(CH$_2$)$_2$-R$_1$=R$_2$=R$_3$=R$_4$=CH$_3$; R$_5$=R$_6$=H; R'=OH; R''=H; B=cyclohexyl; R=—CO$_2$H A suspension of 3.42 g (10 mmoles) of 2-[(5,5,8,8-tetramethyl-5,6,7,8-tetrahydro-2-naphthyl) carbonyl]cyclohexane carboxylic acid, described in Example III, and 10 g of powdered zinc (0.15 mole) in 150 cm$^3$ of a 2.5M aqueous soda solution is heated at reflux for 7 hours. After cooling to +5° C., the reaction mixture is neutralized with 60 cm$^3$ of 6N HCl and then acidified to pH of about 3 by the addition of 20 cm$^3$ of glacial acetic acid. The mixture is then extracted with ethyl ether [2×150 cm$^3$). The ether phase is thoroughly washed with water, dried on sodium sulfate and evaporated to dryness. The resulting solid is taken up in 50 cm$^3$ of hexane, filtered, washed again twice with 40 cm$^3$ of hexane and dried under a vacuum at 40° C. 2.9 g of 2-[(5,5,8,8-tetramethyl-5,6,7,8-tetrahydro-2-naphthyl) hydroxymethyl]cyclohexane carboxylic acid are obtained in the form of a white solid whose melting point is 186° C.

The IR and NMR$^1$H 250 MHz spectra conform to the expected structure.

Elemental Analysis $C_{22}H_{32}O_3$.

|  | C | H | O |
|---|---|---|---|
| Calculated | 76.70 | 9.36 | 13.93 |
| Found | 76.66 | 9.26 | 13.95 |

EXAMPLE XXII

Preparation of sodium 2-[(5,5,8,8-tetramethyl-5,6,7,8-tetrahydro-2-naphthyl)-hydroxymethyl]cyclohexane carboxylate Compound of formula I wherein A=—(CH$_2$)$_2$—; R$_1$=R$_2$=R$_3$=R$_4$=CH$_3$; R$_5$=R$_6$=H; R'=OH; R''=H; B=cyclohexyl; R=CO$_2^\ominus$Na$^\oplus$ 344.48 mg (1 mmole) of 2-[(5,5,8,8-tetramethyl-5,6,7,8-tetrahydro-2-naphthyl)hydroxymethyl cyclohexane carboxylic acid, as described in Example XXI, are suspended in 100 cm$^3$ of bipermuted water. 10 cm$^3$ of 0.1N aqueous soda (1 mmole) are added and the mixture is stirred for 30 minutes in an ultrasonic bath. The resulting solution is evaporated to dryness under reduced pressure. 50 cm$^3$ of anhydrous toluene are added and the mixture is again evaporated to dryness. After drying under a vacuum of 80° C., 0.36 g of sodium 2-[(5,5,8,8-tetramethyl-5,6,7,8-tetrahydro-2-naphthyl)

hydroxymethyl]cyclohexane carboxylate is obtained in the form of a white solid whose melting point is 260° C.

EXAMPLE XXIII

Preparation of 2-[(5,5,8,8-tetramethyl-5,6,7,8-tetrahydro-2-naphthyl)-methyl]benzoic acid Compound of formula I wherein $A = -(CH_2)_2-$; $R_1 = R_2 = R_3 = R_4 = CH_3$; $R_5 = R_6 = H$; $R' = R'' = H$; B=phenyl; and $R = CO_2H$ A mixture of 6 g of zinc, 0.6 g mercuric chloride, 9 cm$^3$ of water and 0.3 cm$^3$ of concentrated HCl is stirred for 10 minutes at ambient temperature. The solution is decanted and the amalgam is rinsed twice with 25 cm$^3$ of water. There are then added 10 cm$^3$ of water, 5 cm$^3$ of concentrated HCl, 8 cm$^3$ of toluene, 8.4 g (0.025 mole) of 2-[(5,5,8,8-tetramethyl-5,6,7,8-tetrahydro-2-naphthyl) carbonyl]benzoic acid, described in Example I. The mixture is heated for 30 hours and reflux with stirring while adding 3 cm$^3$ of concentrated HCl every 6 hours. 20 cm$^3$ of toluene are added and the mixture is filtered cold. The amalgam is washed three times with 40 cm$^3$ of toluene. The filtrate is transferred to a decanting ampoule and the toluene phase is separated, washed with water, dried on sodium sulfate and then concentrated under reduced pressure. The isolated crude product is recrystallized in a mixture of heptane and isopropyl ether. After drying, 6.6 g of white crystals of 2-[(5,5,8,8-tetramethyl-5,6,7,8-tetrahydro-2 naphthyl) methyl]benzoic acid are obtained whose melting point is 136° C.

The NMR$^1$H 80 MHz spectrum conforms to the expected structure.

Elemental Analysis: $C_{22}H_{26}O_2$.

|  | C | H | O |
|---|---|---|---|
| Calculated | 81.95 | 8.13 | 9.92 |
| Found | 82.14 | 8.16 | 9.79 |

EXAMPLE XXIV

Preparation of ethyl 2-[(5,5,8,8-telramethyl-5,6,7,8-tetrahydro-2-naphthyl)-carboxyl]benzoate Compound of formula I wherein $A = -(CH_2)_2-$; $R_1 = R_2 = R_3 = R_4 = CH_3$; $R_5 = R_6 = H$; $R', R'' = oxo$; B=phenyl; and $R = -CO_2C_2H_5$ A solution of 8.41 g (0.025 mole) of 2-[(5,5,8,8-tetramethyl-5,6,7,8-tetrahydro-2-naphthyl) carbonyl]benzoic acid, described in Example I, in 300 cm$^3$ of ethyl alcohol containing 0.4cm$^3$ of 98% sulfuric acid is heated for 14 hours at reflux. The solution is then concentrated under reduced pressure and the resulting crude ester is dissolved in 300 cm$^3$ of ethyl ether. The ether solution is washed with sodium bicarbonate and then with water, dried on sodium sulfate and evaporated to dryness. After drying, 7.9 g of ethyl 2-[(5,5,8,8-tetramethyl-5,6,7,8-tetrahydro-2-naphthyl) carbonyl]benzoate are obtained in the form of a colorless oil which slowly crystallizes at ambient temperature to give a white solid whose melting point is 58°-59° C.

The IR and NMR$^1$H 80 MHz spectra conform to the expected structure.

Elemental Analysis: $C_{24}H_{28}O_3$.

|  | C | H | O |
|---|---|---|---|
| Calculated | 79.09 | 7.74 | 13.17 |
| Found | 79.19 | 7.75 | 13.02 |

EXAMPLE XXV

Preparation of zinc 2-[(5,5,8,8-tetramethyl-5,6,7,8-tetrahydro-2-naphthyl) carbonyl]benzoate Compound of formula I wherein $A = -(CH_2)_2-$; $R_1 = R_2 = R_3 = R_4 = CH_3$; $R_5 = R_6 = H$; $R', R'' = oxo$; B=phenyl; and $R = -CO_2^{\oplus} \frac{1}{2} Zn^{6\ominus}$ 368.5 mg (1.1 mmoles)of 2-[(5,5,8,8-tetramethyl-5,6,7,8-tetrahydro-2-naphthyl) carbonyl]benzoic acid, described in Example I are suspended in 150 cm$^3$ bipermuted water. 11 cm$^3$ (1.1 mmoles) of 0.1N soda are added and the mixture is stirred in an ultrasonic bath until the components are dissolved (30 minutes). To the resulting solution of the sodium salt, 157.5 mg (0.548 mmole) of zinc sulfate·7H$_2$O are added and the zinc salt, formed by transalification, precipitates. It is filtered, washed with water and dried under a vacuum at 70°-80° C. 0.4 g of zinc 2-[(5,5,8,8-tetramethyl-5,6,7,8-tetrahydro-2-naphthyl) carbonyl]benzoate is obtained in the form of a white solid that becomes vitreous at about 155° C.

EXAMPLE XXVI

Preparation of zinc 2-[(5,5,8,8-tetramethyl-5,6,7,8-tetrahydro-2-naphthyl) carbonyl]cyclohexane carboxylate Compound of formula I where in $A = -(CH_2)_2-$; $R_1 = R_2 = R_3 = R_4 = CH_3$; $R_5 = R_6 = H$; $R', R'' = oxo$; B=cyclohexyl; and $R = -CO_2^{\oplus} \frac{1}{2} Zn^{\ominus}$ 381.7 mg (1.115 mmoles) of 2-[(5,5,8,8-tetramethyl-5,6,7,8-tetrahydro-2-naphthyl) carbonyl]cyclohexane carboxylic acid, described in Example III, are suspended in 150 cm$^3$ of bipermuted water. 11.2 cm$^3$ (1.12 mmoles) of 0.1N soda are added and the mixture is stirred in an ultrasonic bath until the components are dissolved (40 minutes). 160.4mg (0.558 mmole) of zinc sulfate·7H$_2$O are added and the precipitate that forms is filtered. After washing with water and drying under a vacuum at 70-80° C., 0.41 g of zinc 2-[(5,5,8,8-tetramethyl-5,6,7,8-tetrahydro-2-naphthyl) carbonyl cyclohexane carboxylate is obtained in the form of a white solid that becomes vitreous at about 135° C.

EXAMPLES OF COMPOSITIONS

Example 1 —Antiseborrheic lotion

| | |
|---|---|
| Absolute alcohol | 59.0 g |
| Propylene glycol | 40.0 g |
| 2-[(5,5,8,8-tetramethyl-5,6,7,8-tetrahydro-2-naphthyl) carbonyl] benzoic acid | 1.0 g |

Example 2—Lotion for combatting oily skin

| | |
|---|---|
| Absolute alcohol | 60.0 g |
| Polyethylene glycol 400 | 39.5 g |
| 2-[(5,5,8,8-tetramethyl-5,6,7,8-tetrahydro-2-naphthyl) carbonyl benzoic acid | 0.5 g |

In this lotion example the active compound can be replaced by 1 g of 2-[(1,1,2,3,3-pentamethyl-5-indanyl) carbonyl] benzoic acid or 0.3 g of 2-[(5,5,8,8-tetramethyl5,6,7,8-tetrahydro-2-naphthyl)

Example 3—Lotion for the care of the face having acne tendencies

| | |
|---|---|
| Absolute alcohol | 42.0 g |
| Propyleneglycol | 24.0 g |
| Purified water | 33.0 g |
| 2-[(5,5,8,8-tetramethyl-5,6,7,8-tetrahydro-2-naphthyl) carbonyl] benzoic acid | 1.0 g |

The active compound can be replaced by 0.5 g of 2[(5,5,8,8-tetramethyl-5,6,7,8-tetrahydro-2-naphthyl) carbonyl] cyclohexane carboxylic acid or 2[(5,5,8,8-tetramethyl-5,6,7,8-tetrahydro-2-naphthyl) hydroxymethyl] cyclohexane carboxylic acid.

Example 4—Gel to combat against oily skin having acne tendencies

| | |
|---|---|
| Carbopol 941 | 0.80 g |
| Absolute alcohol | 32.15 g |
| Propylene glycol | 35.00 g |
| Butylhydroxytoluene | 0.02 g |
| Butylhydroxyanisole | 0.03 g |
| Triethanolamine, 20% | 1.00 g |
| Purified water | 30.00 g |
| 2-[(5,5,8,8-tetramethyl-5,6,7,8-tetrahydro-2-naphthyl) carbonyl] benzoic acid | 1.00 g |

Example 5—Gel to combat against oily skin having acne tendencies

| | |
|---|---|
| Klucel H (cellulosic derivative) | 1.00 g |
| Absolute alcohol | 70.00 g |
| Propylene glycol | 28.45 g |
| Butylhydroxytoluene | 0.02 g |
| Butylhydroxyanisole | 0.03 g |
| 2-[(5,5,8,8-tetramethyl-5,6,7,8-tetrahydro-2-naphthyl) carbonyl] benzoic acid | 0.50 g |

The active compound can be replaced by the same amount of 2-[(1,1,2,3,3-pentamethyl-5-indanyl) carbonyl] benzoic acid or 2-[(5,5,8,8-tetramethyl-5,6,7,8-tetrahydro-2-naphthyl carbonyl] cyclohexane carboxylic acid or even 2-[(5,5,8,8-tetramethyl-5,6,7,8-tetrahydro-2-naphthyl) hydroxymethyl] cyclohexane carboxylic acid.

Example 6—Cream for oily skin

| | |
|---|---|
| Glycol monostearate | 4.00 g |
| Cetyl alcohol | 3.50 g |
| Myrj 53 (polyethylene glycol stearate oxyethylenated with 50 moles of ethylene oxide, sold by Atlas) | 3.00 g |
| Capric/caprylic triglyceride | 22.00 g |
| Propylparahydroxybenzoate | 0.15 g |
| Butylhydroxytoluene | 0.02 g |
| Butylhydroxyanisole | 0.03 g |
| Propylene glycol | 8.00 g |
| 2-[(5,5,8,8-tetramethyl-5,6,7,8-tetrahydro-2-naphthyl) carbonyl] benzoic acid | 2.00 g |
| Water, sufficient amount for | 100 g |

Example 7—Stick (coloring) for application to defined areas of the skin

| | |
|---|---|
| Petrolatum | 19.40 g |
| Cosbiol (perhydrosqualene) | 40.00 g |
| Solid paraffin | 2.00 g |
| Carnauba wax | 2.00 g |
| Ozokerite | 9.00 g |
| Butylhydroxytoluene | 0.05 g |
| Butylhydroxyanisole | 0.05 g |
| Red iron oxide | 0.50 g |
| Yellow iron oxide | 1.50 g |
| Brown iron oxide | 2.50 g |
| Titanium oxide | 20.00 g |
| 2-[(5,5,8,8-tetramethyl-5,6,7,8-tetrahydro-2-naphthyl) carbonyl] benzoic acid | 1.00 g |
| Rice starch | 2.00 g |

The active compound can be replaced by 0.5 g of 2-[(5,5,8,8-tetramethyl-5,6,7,8-tetrahydro-2-naphthyl) carbonyl] cyclohexane carboxylic acid.

What is claimed is:

1. A bicyclic aromatic compound having the formula $$\begin{array}{c} R_1 \quad R_2 \quad R_5 \quad R' \quad R'' \quad R \\ A \qquad\qquad\qquad B \\ R_3 \quad R_4 \quad R_6 \end{array} \quad (R)$$

wherein
$R_1$, $R_2$, $R_3$ and $R_4$ each independently represent hydrogen or lower alkyl, at least two of the $R_1$-$R_4$ radicals being other than hydrogen,
A represents methylene or dimethylene, substituted or not by lower alkyl; when A represents dimethylene, $R_1$ and $R_3$ together can form a methylene or dimethylene radical,
$R_5$ and $R_6$ represent hydrogen, halogen, lower alkyl, lower alkoxy or hydroxy,
R' and R'' together form an oxo radical,
B represents cyclohexyl, cyclohexenyl, cyclohexadienyl or phenyl, substituted or not,
R represents $-CH_2OH$ or $-COR_7$,
$R_7$ represents hydrogen, $-OR_8$ or $$-N\begin{matrix} r' \\ r'' \end{matrix},$$

$R_8$ represents hydrogen, alkyl having 1-20 carbon atoms, monohydroxyalkyl, polyhydroxyalkyl or aryl or aralkyl,
r' and r'' represent hydrogen, lower alkyl, monohydroxyalkyl optionally interrupted by a heteroatom polyhydroxyalkyl, aryl or benzyl or the residue of amino acid, or r' and r'' taken together form a heterocycle, and
the salts of said compounds of formula I, their optical isomers and the tautomeric forms of the compound of formula I with the exception of 2-((5,8-methano-5,6,7,8-tetrahydro-2-naphthyl) carbonyl) benzoic acid.

2. The compound of claim 1 wherein said lower alkyl and said alkyl having 1-20 carbon atoms are selected from the group consisting of methyl, ethyl, propyl, butyl, 2-ethylhexyl, octyl, dodecyl, hexadecyl and octadecyl.

3. The compound of claim 1 wherein said monohydroxyalkyl is 2-hydroxyethyl, 2-hydroxypropyl or 2-hydroxyethoxyethyl.

4. The compound of claim 1 wherein said polyhydroxyalkyl is 2,3-dihydroxypropyl, 1,3-dihydroxy-2-propyl or the residue of pentaerythriol.

5. The compound of claim 1 wherein said lower alkoxy is methoxy, isopropyl, or butoxy.

6. The compound of claim 1 wherein B is phenyl substituted by lower alkyl, halogen or alkoxy at position 3, 4, 5, or 6.

7. The compound of claim 1 wherein r' and r" taken together with the nitrogen atom to which they are attached form a piperidino, piperazino, morpholino, pyrrolidino or 4-(2-hydroxyethyl) piperazino radical.

8. The compound of claim 1 having the formula

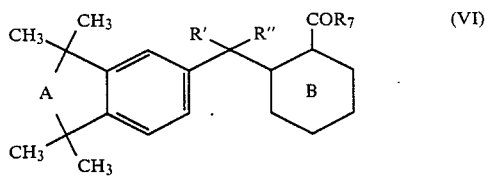

wherein
R' and R" taken form an oxo radical,
A represents —(CH$_2$)$_2$or

B represents phenyl or cyclohexyl,
R$_7$ represents —OR$_8$ or

R$_8$ represents hydrogen or alkyl having 1-12 carbon atoms
r' represents hydrogen or monohydroxyalkyl, and
r" represents alkyl having 1-6 carbon atoms, monohydroalkyl optionally interrupted by a heteroatom or polyhydroalkyl,
or r' and r" taken together with the nitrogen atom to which they are attached form a 4-(2-hydroxyethyl) piperazinyl radical, and
the salts of the compounds of formula Iv.

9. The compound of claim 1 selected from the group consisting of:
2-[(5,5,8,8-tetramethyl-5,6,7,8-tetrahydro-2-naphthyl) carbonyl] benzoic acid,
2-[(1,1,2,3,3-pentamethyl-5-indanyl) carbonyl] benzoic acid,
2-[(5,5,8,8-tetramethyl-5,6,7,8-tetrahydro-2-naphthyl) carbonyl] cyclohexane carboxylic acid,
2-[(1,1,2,3,3-pentamethyl-5-indanyl) carbonyl]-1-cyclohexene-1-carboxylic acid,
2-[(1,4-dimethoxy-5,8-methano-5,6,7,8-tetrahydro-2-naphthyl) carbonyl] benzoic acid,
2'-ethylhexyl-2[(5,5,8,8-tetramethyl-5,6,7,8-tetrahydro-2-naphthyl) carbonyl] benzoate,
ethyl 2-[(1,1,2,3,3-pentamethyl-5-indanyl) carbonyl] benzoate,
methyl 2-[(5,5,8,8-tetramethyl-5,6,7,8-tetrahydro-2-naphthyl) carbonyl]benzoate,
N-ethyl 2-[(5,5,8,8-tetramethyl-5,6,7,8-tetrahydro-2-naphthyl) carbonyl] benzamide,
N,N-di-n-butyl 2-[(5,5,8,8-tetramethyl-5,6,7,8-tetrahydro-2-naphthyl) carbonyl] benzamide,
2-[(5,5,8,8-tetramethyl-5,6,7,8-tetrahydro-2-naphthyl) carbonyl]benzaldehyde,
sodium 2-[(5,5,8,8-tetramethyl-5,6,7,8-tetrahydro-2-naphthyl) carbonyl] benzoate,
sodium 2-[(5,5,8,8-tetramethyl-5,6,7,8-tetrahydro-2-naphthyl) carbonyl] cyclohexane carboxylate,
2-[(1,1,3,3-tetramethyl-5-indanyl) carbonyl] benzoic acid,
2-[1,1,2,3,3-pentamethyl-5-indanyl) carbonyl] cyclohexane carboxylic acid,
N,N-di(2-hydroxyethyl) 2-[(5,5,8,8-tetramethyl-5,6,7,8-tetrahydro-2-naphthyl) carbonyl] benzamide,
N-4,-(2-hydroxymethyl)piperazino 2-[(5,5,8,8-tetramethyl-5,6,7,8-tetrahydro-2-naphthyl) carbonyl] benzamide,
ethyl 2-[(5,5,8,8-tetramethyl-5,6,7,8-tetrahydro-2-naphthyl) carbonyl] cyclohexane carboxylate,
ethyl 2-[(5,5,8,8-tetramethyl-5,6,7,8-tetrahydro-2-naphthyl) carboxyl] benzoate,
zinc 2-[(5,5,8,8-tetramethyl-5,6,7,8-tetrahydro-2-naphthyl) carbonyl] benzoate and
zinc 2-[(5,5,8,8-tetramethyl-5,6,7,8-tetrahydro-2-naphthyl) carbonyl] cyclohexane carboxylate.

10. A cosmetic composition comprising in a cosmetically acceptable vehicle at least one compound of claim 1.

11. The cosmetic composition of claim 10 wherein said compound is present in an amount ranging from 0.005 to 5 percent by weight based on the total weight of said composition.

12. The cosmetic composition of claim 10 wherein said compound is present in an amount ranging from 0.01 to 1 percent by weight based on the total weight of said composition.

13. A pharmaceutical composition in a pharmaceutically acceptable vehicle at least one compound of claim 1, said vehicle being suitable for enteral, parenteral, topical or ocular adminstration.

14. The pharmaceutical composition of claim 13, wherein said vehicle is suitable for topical application and said compound is present in an amount ranging from 0.01 to 10 percent by weight based on the total weight of said composition.

15. The composition of claim 14 wherein said compound is present in an amount ranging from 0.1 to 5 percent by weight based on the total weight of said composition.

* * * * *